US008379198B2

(12) United States Patent
Miller et al.

(10) Patent No.: US 8,379,198 B2
(45) Date of Patent: Feb. 19, 2013

(54) CHIRAL PLASMONIC STRUCTURES FOR MEDIATING CHEMICAL TRANSFORMATION AND DETECTION OF MOLECULES WITH SPATIAL CHIRALITY

(75) Inventors: Michael A. Miller, San Antonio, TX (US); Diana L. Strickland, San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 212 days.

(21) Appl. No.: 13/052,940

(22) Filed: Mar. 21, 2011

(65) Prior Publication Data

US 2011/0235032 A1    Sep. 29, 2011

Related U.S. Application Data

(60) Provisional application No. 61/317,952, filed on Mar. 26, 2010.

(51) Int. Cl.
*G01J 3/44* (2006.01)
(52) U.S. Cl. .................................. 356/301; 422/186.04
(58) Field of Classification Search .................. 356/301; 422/186.04
See application file for complete search history.

(56) References Cited

U.S. PATENT DOCUMENTS

2011/0180386 A1    7/2011    Miller

OTHER PUBLICATIONS

Govorov et al, Theory of Circular Dichroism of Nanomaterial Comprising Molecules and Nanocrystals: Plasmon Enhancement..., Feb. 25, 2010, Nano Letters, 2010, 10, 1374-1392.*
Valev et al, Asymmetric Optical Second-Harmonic Generation from Chiral G-Shaped Gold Nanostructures, Mar. 2010, Physical Reveiw Letters, The American Physical Society.*
Fedotov et al, Asymmetric Tranmission of Light and Enantiomerically Sensitive Plasmon Resonance in Planar Chiral Nanostructures, Jun. 20, 2007, Nano Letters, American Chemical Society.*
Miller et al., "The Role of Low-Frequency Plasmons in Molecular Adsorption: A Theoretical and Spectroscopic Study of Gold and Titanium Compounds," J. Phys. Chem. C 2008, 112, 6939-6946.
Kresin, "Photoabsorption of small metal clusters: Surface and volume modes," Physical Review B Condensed Matter, Third Series, vol. 42, No. 6, Aug. 15, 1990-II pp. 3247-3252.
Wang, et al., "Collective electronic excitations and their damping in small alkali clusters," Chemical Physics Letters, vol. 205, No. 6, Apr. 23, 1993, pp. 521-528.
Mohr et al., "Hydrogenation properties of supported nanosized gold particles," Science Progress (2001), 84 (4), 311-334, pp. 311-334.
Egri, "The Internal Structure of Plasmons," Z. Phys. B—Condensed Matter, 53, 183-189 (1983).
Haynes, et al., "Nanosphere Lithography: A Versatile Nanofabrication Tool for Studies of Size-Dependent Nanoparticle Optics," J. Phys. Chem. B 2001, 105, 5599-5611.
Ozbay, "Plasmonics: Merging Photonetics and Electronics at Nanoscale Dimensions," Science vol. 311, Jan. 13, 2006, pp. 189-193.
Smekal, "Zuschriften und vorlaufige Mitteilungen." Naturwissenschaften,1923, 11, 873.

(Continued)

*Primary Examiner* — Layla Lauchman
(74) *Attorney, Agent, or Firm* — Grossman, Tucker et al

(57) ABSTRACT

Three-dimensional metal dielectric structures are disclosed with chiral symmetry that elicit surface plasmons. The plasmons may have propagational circular polarization wherein the frequency of such propagating plasmons may be tuned by design to couple with the electronic transitions or fundamental vibrations, including phonons, of a molecular species. The plasmon-molecule coupling, combined with the propagational polarization afforded by the chiral structure may be further exploited to mediate the chemical transformations involving molecules with spatial chirality and/or to detect molecules with spatial chirality.

23 Claims, 14 Drawing Sheets

OTHER PUBLICATIONS

Raman, "A weekly journal of science," Nature, No. 3066, vol. 122, Aug. 4, 1928, p. 169.
Leiro, et al., "Study of plasmon structure in XPS spectra of silver and gold," J. Phys. F: Met. Phys. 13 (1983) 215-221.
Pendry, et al., "Mimicking Surface Plasmons with Structured Surfaces," Science vol. 305, Aug. 6, 2004, pp. 847-848.
Hibbins, et al., "Experimental Verification of Designer Surface Plasmons," Science vol. 308, Apr. 29, 2005, pp. 670-672.
Pendry, et al., "Extremely Low Frequency Plamons in Metallic Mesostructures," Physical Review Letters, vol. 76, No. 25, Jun. 17, 1996, pp. 4773-4776.
Shir, et al., "Three-Dimensional Nanofabrication with Elastomeric Phase Masks," J. Phys. Chem. B 2007, 111, 12945-12958.
Jeon, et al., "Molded transparent photopolymers and phase shift optics for fabricating three dimensional nanostructures," Optics Express, vol. 15, No. 10, May 14, 2007, pp. 6358-6366.
Gansel, et al., "Gold Helix Photonic Metamaterial as Broadband Circular Polarizer," Science vol. 325, Sep. 18, 2009, pp. 1513-1515.
Norton, et al., "Silica Nanosprings—A Novel Nanostructured Material for Hydrogen Storage," Clean Technology 2009, pp. 202-205.
Belov, et al., "Subwavenlenght microwave imaging using an array of parallel conducting wires as a lens," Physical Review B 73, 033108 (2006) (4 pages).

* cited by examiner

CHIRAL PLASMONIC STRUCTURES FOR MEDIATING CHEMICAL TRANSFORMATION AND DETECTION OF MOLECULES WITH SPATIAL CHIRALITY

CROSS REFERENCE TO RELATED APPLICATIONS

The present application claims the benefit of the filing date of U.S. Provisional Application Ser. No. 61/317,952, filed Mar. 26, 2010, the teachings of which are incorporated herein by reference.

FIELD OF THE INVENTION

This disclosure relates to 3-D structures with chiral symmetry that elicit surface plasmons. The plasmons may have propagational circular polarization wherein the frequency of such propagating plasmons may be tuned by design to couple with the electronic transitions or fundamental vibrations, including phonons, of a molecular species. This plasmon-molecule coupling, combined with the propagational polarization afforded by the chiral structure, may be further exploited to, e.g., mediate the catalysis of chemical transformations involving molecules with spatial chirality and/or to detect molecules with spatial chirality.

BACKGROUND

Plasmons are understood to be a quantum of plasma oscillation. Plasmons may be classically described as an oscillation of a free electron density against a fixed positive ion in a metal. Electrons may move in one direction (uncovering positive ions) in the presence of an external electric field until they cancel the field inside the metal. In the absence of the electric field the electrons may shift and be repelled by one another and attracted to the positive ions. The electrons may then oscillate back and forth at the plasma frequency until energy may be lost in some kind of resistance or damping. Plasmons are the quantization of this type of oscillation.

Surface plasmons, which may also be known as surface plasmon polaritons (SPPs), are surface electromagnetic waves that propagate in a direction parallel to a metal/dielectric or metal/vacuum interface. As the wave is on the boundary of the metal and external medium (air or water for example), these oscillations may be very sensitive to any change of this boundary, such as the adsorption of molecules to the metal interface.

SUMMARY

The present invention utilizes photon (external field) and oscillator (surface induced) excitation of SPPs and the effects that the SPPs' local fields provide on chemical transformations when molecules, including molecules of specific spatial chirality, are adsorbed on and/or in proximity to specially-tuned 3-D plasmonic structures having chiral spatial properties.

The present invention also utilizes such 3-D plasmonic structures and SPPs elicited therewith as a method for detecting the presence of same molecules when combined with spectroscopic techniques. The spectral techniques may include surface enhanced Raman spectroscopy (SERS), near-field scanning optical microscopy (NSOM), atomic force microscopy (AFM), spectral ellipsometry, and surface plasmon resonance spectroscopy (SPRS). The 3-D chiral plasmonic structures may be tailored to elicit SPPs whose frequency is in resonance with one or more electronic transitions or fundamental vibrational modes of selected molecules. The electric and magnetic components of the propagating SPPs therefore undergo polarization in a specific direction as dictated by the chirality of the 3-D chiral plasmonic structure.

In one exemplary embodiment, the present disclosure is therefore directed at a structure comprising a metal dielectric possessing spatial chirality capable of eliciting surface plasmon modes at selected frequencies to provide a surface bound electric field that exhibits propagational polarization when excited by a circularly polarized external source and/or a vibrational dipole created by a molecule adsorbed on the metal dielectric surface, the molecule having a spatial chirality. The surface-bound electric field is then capable of coupling with electronic, vibrational, or phonon transitions of said molecule wherein the propagational polarization of the surface-bound electric field of the plasmon created by the chiral metal dielectric couples with the chirality of said molecule and the molecule then undergoes a chemical transformation.

In another exemplary embodiment the present disclosure is directed at a process for causing a chemical transformation of a molecule on the surface of structure by first supplying a metal dielectric possessing spatial chirality capable of eliciting surface plasmon modes at selected frequencies to provide a surface bound electric field that exhibits propagational polarization when excited by a circularly polarized external source and/or a vibrational dipole created by a molecule adsorbed on the metal dielectric surface, the molecule having a spatial chirality. This may then be followed by coupling the surface bound electric field with the molecule on the surface of the metal dielectric structure such that the propagational polarization of the surface bound electric field couples with the chirality of said molecule and chemically transforms the molecule.

In a third exemplary embodiment, the present disclosure is directed at a process for spatially resolving images of individual enantiomers of a racemic mixture by first supplying a metal dielectric structure possessing spatial chirality capable of eliciting surface plasmon modes at selected frequencies to provide a surface bound electric field that exhibits propagational polarization when excited by a circularly polarized external source and/or a vibrational dipole created by a racemic mixture of molecules adsorbed on or near the metal dielectric surface, the molecules having spatial chirality. This may then be followed by coupling the surface bound electric field with the molecule on the surface of the metal dielectric structure such that the propagational polarization of the surface bound electric field couples with the chirality of said molecule and detecting the proportion and position of enantiomers in the racemic mixture.

DETAILED DESCRIPTION

Hybrid materials consisting of at least one metal (e.g., gold, silver, copper etc.) and one dielectric (e.g., polymer, ceramic, or air), which are engineered to form an extended structure of smaller repeating units, exhibit unique properties when they interact with an electromagnetic (EM) field, such as light, at wavelengths often much larger than the unit structure. These hybrid materials may be understood herein as "metamaterials" as a consequence of their indicated compositional framework. A dielectric herein may be understood as any material that is an electric insulator, and may only polarize within a given electrical field.

An important phenomenon that emerges from certain types of metamaterial structures is the proficiency in which surface plasmon-polaritons (SPPs) are excited therefore providing a surface plasmon mode. Plasmons may be attributed to the collective oscillations of free electrons in the metal-component of the metamaterial structure which in turn may then generate a spatially-intense oscillating EM field confined to the interface between the metal surface and the dielectric.

The theoretical framework describing the interaction between photon- and dipole excited surface plasmon polaritons (SPPs) and the vibrational wavefunctions demonstrates that such coupling may now lead to enhanced binding interactions of surface molecules and/or catalysis of chemical transformations. Experimental validation of this plasmon-mediated chemical binding and catalysis effects has remained elusive until now because metamaterials that elicit SPPs at frequencies of molecular vibrations (infrared) were not experimentally accessible. Infrared herein may be understood as electromagnetic radiation with a wavelength between 0.7 and 300 micrometers, which equates to a frequency range between approximately 1 and 430 THz.

It may now be shown through modeling and simulations that, under certain conditions, the excitation within the infrared (e.g. at 132 THz) SPPs can be realized, preferably from structures consisting of 3-D metal-wire grids with periodic cubic symmetry. It is further shown that the local electric field of the SPP may be several orders of magnitude higher than the amplitude of the incident field. The present disclosure is therefore directed towards employing such surface plasmons to influence chemical transformations of an exposed molecule or molecules.

Figure 1:
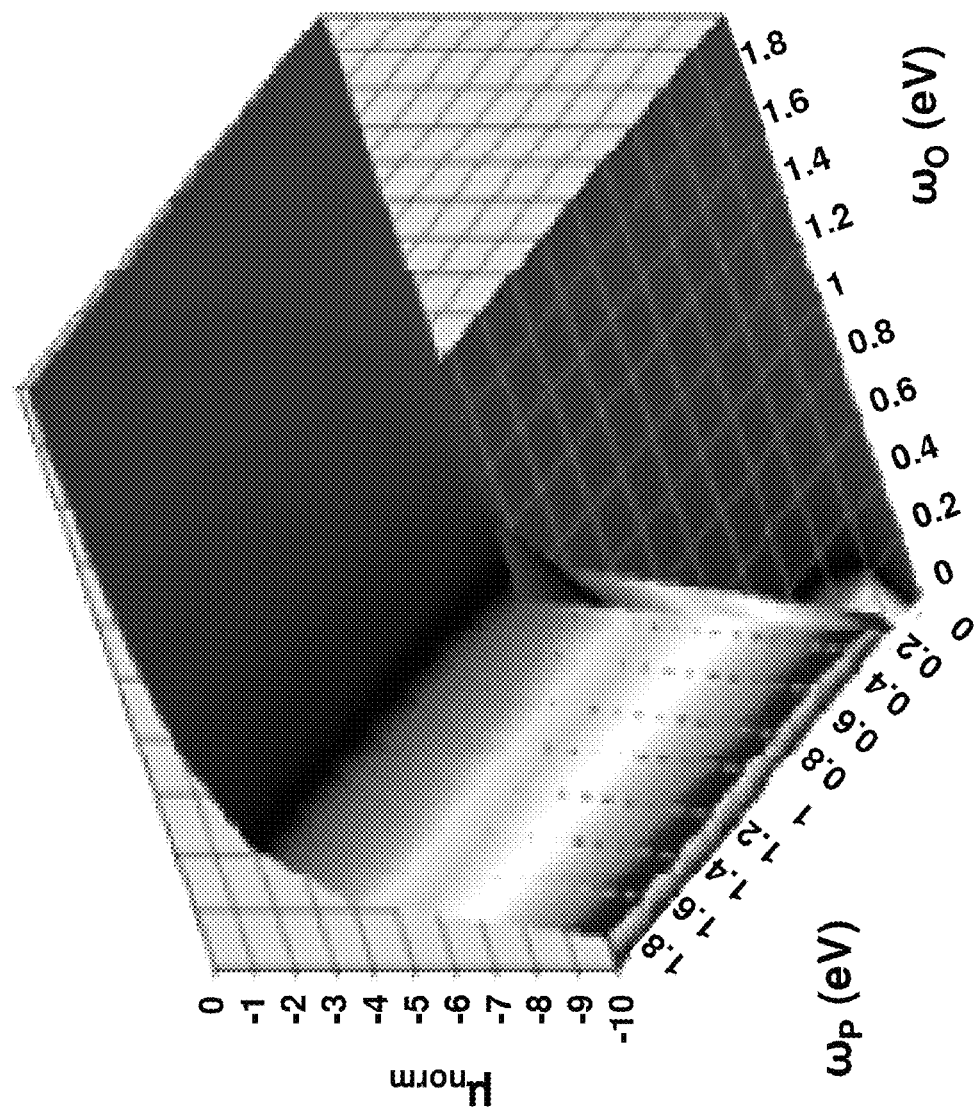
FIG. 1 illustrates the dependence of the normalized surface-induced dipole moment ($\mu_{norm}$) on the plasmon frequency ($\omega_p$) and excitation frequency ($\omega_0$).

The surface induced vibrational dipole ($\mu_{norm}$) in a molecule on the surface of a metal can couple with and excite SPPs such that $\mu_{norm}$ rapidly increases as the excitation frequency of the molecule decreases, falling into a coulombic trap (i.e., large gradient in $\mu_{norm}$) as vibrational transitions comparable to plasmon frequencies are approached (FIG. 1). Such is the case when the frequency of a molecular transition is degenerate with the plasmon frequency ($\omega_0 = \omega_p$). The implication of this theoretical result is that the vibrational dipole couples with the SPP on resonance, and the electric field associated with this vibrational coupling is dominated by the SPP.

Figure 2:
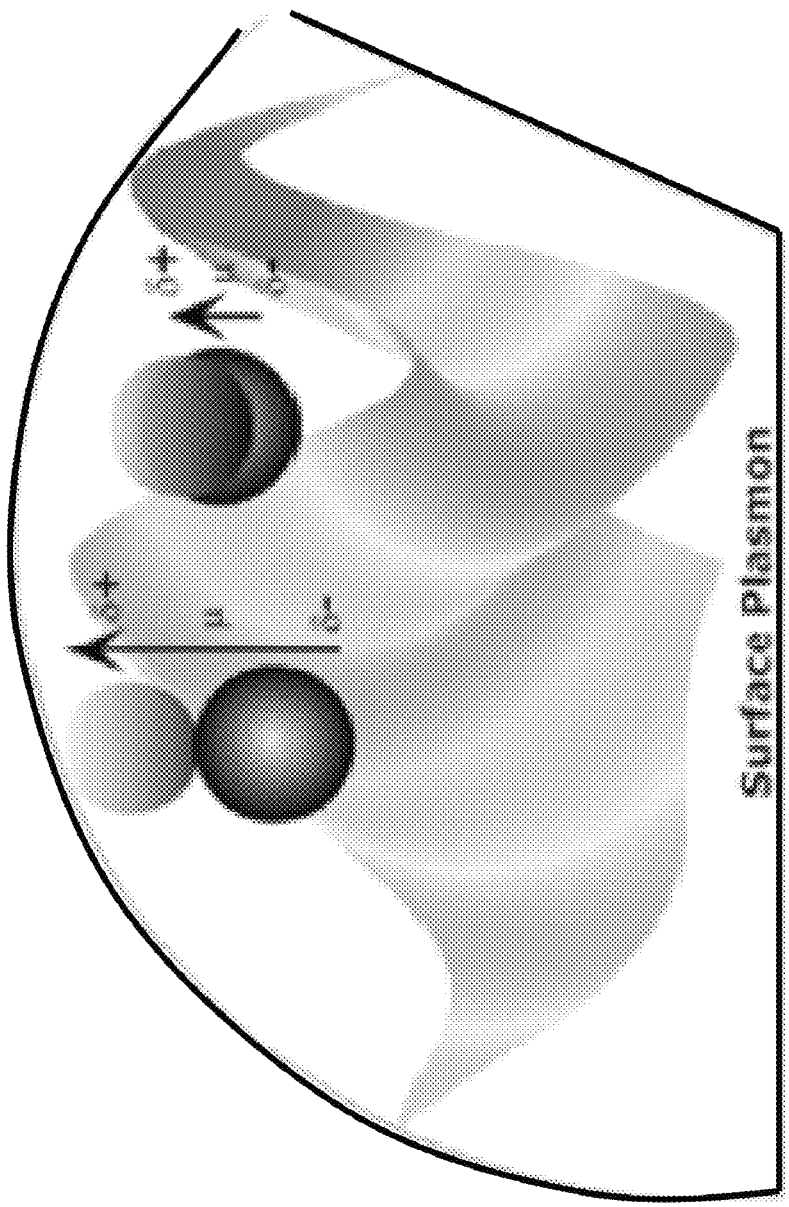
FIG. 2 illustrates the coupling of a surface-induced vibrational dipole of a quadrupolar molecule and surface plasmon.

This effect is now illustrated in FIG. 2 for an isotropic wavefunction of the SPP for collective excitation from the ground state at a finite temperature. Specifically, FIG. 2 shows the coupling of a surface-induced vibrational dipole of a quadrupolar molecule and a surface plasmon. As additional molecules are adsorbed to the surface, the van der Waals interactions among surface molecules are significantly attenuated by the electric field of the surface plasmon, and there arises a distance dependence of this attenuated field spread over the surface of the metal. Under certain conditions as might be the case for an external radiational field, such as a blackbody source, the SPP field attenuation may be strong enough to mediate a chemical transformation, such as dissociation. For $CO_2$ as an example, the on-resonance condition is near 2349 $cm^{-1}$ (0.291 eV) for the ground-state asymmetric stretching mode, which is far lower than the lowest plasmon frequency of most pure metals (e.g., gold: $\omega_p = 2.7$ eV). This dilemma can now be overcome by considering mesoscale architectures which give rise to SPPs with relatively low frequencies.

The present disclosure now stands directed at the fabrication of 3-D metamaterial structures with chirality that may be designed, via computational simulations, to elicit SPPs whose frequency is in resonance with one or more electronic, vibrational, or phonon transitions of a molecule of interest adsorbed on, or in proximity to, the structure. Chirality is in this context defined as any 3-D structure whose mirror image, essentially the spatial orientation and handedness of the image, cannot be superimposed.

In addition to SPPs being in resonance with electronic, vibrational, or phonon transitions of a molecule, a further aspect of the present disclosure afforded by the chirality of the structure is that both the electric (E) and magnetic (H) field components of the SPP may undergo propagational polarization; for example, right-handed or left-handed circular polarization. Thus, molecules with spatial chirality adsorbed on, or in proximity to, the chiral 3-D structure may couple on resonance with both the SPP's strong, localized electric field and the polarization of that field when, in particular, the direction of the latter is coincident with the direction of optical activity of the corresponding molecule.

In the case of subjecting 3-D metamaterials with chirality to an external field exhibiting circular polarization, wherein the frequency of the external field elicits SPPs in the chiral structure of the 3-D metamaterials that in-turn are resonant with one or more electronic, vibrational, or phonon transitions of a chiral molecule adsorbed on, or in proximity to, the 3-D metamaterial structure, the polarization of the external field may be made to be either in the same or opposite direction as the chirality of the said structure. Different orders of multipoles (i.e., dipole, quadrupole, hexapole, octapole, etc.) in the electric field of the SPP can arise depending on whether the circular polarization of the external field is in the same (ortho) or opposite (para) direction as the chirality of the structure. These combinations are illustrated in Table 1.

TABLE 1

Relationship between the circular polarization of the external field and the chirality (handedness) of the 3-D plasmonic structure for ortho and para combinations, and the effect on the phase of the electric field of the SPP.

| Field/Structure Circular Polarization | Ortho | Phase of E | Para | Phase of E |
|---|---|---|---|---|
| External Field | ↻ | Dipole | ↻ | Multipole |
| Structural Chirality | ↻ | | ↺ | |
| External Field | ↺ | Dipole | ↺ | Multipole |
| Structural Chirality | ↺ | | ↻ | |

It may now be demonstrated that a chiral molecule on, or in close proximity to, a chiral plasmonic structure will experience a combined perturbation from resonant coupling of the SPP with one or more electronic, vibrational, or phonon states of the chiral molecule, plus the propagational polarization of the SPP. This combined coupling can be further discriminated according to the dipole and multipole phases of the SPP's electric field generated by choosing ortho or para combinations.

For example, a chiral molecule possessing optical activity in the same direction as the ortho combination, whose electronic, vibrational, or phonon transitions are resonant with the SPP's electric field, will be further affected by the propagational polarization of the SPP, which is coincident with the direction of the molecule's optical activity, and the dipole phase vortices generated by the SPP's electric field. By comparison, the same chiral molecule in resonant coupling with the SPP will be affected in a different way for the para combination due to the propagational polarization of the SPP and multipole phase vortices generated by the SPP's electric field.

It can be appreciated from the foregoing description that one aspect of this disclosure is that the precise nature in which a chiral molecule interacts in resonance with the SPP's electric field, its propagational polarization along the chiral structure, and phase vortices generated therein due to ortho or para combinations, can be used to sense, excite, or transform the molecule with precision.

Transforming a molecule in the present context may also involve a selective chemical transformation of one of two chiral molecules (a.k.a. enantioselective) present on, or in close proximity to, the chiral plasmonic structure. A chemical transformation herein may be understood to include, but not be limited to, any transition of a selected molecule with respect to its electron bonding behavior or characteristics and/or bonding configurations (e.g. single versus double bonds and/or the formation of new bonds within the elements present or between the chemical compounds present). Chemical transformation herein may also include transitions to a metastable state (i.e. a state where the structure under consideration is in a relatively unstable state or first state and seeks to transition to a relatively more stable state or second state). An example of the metastable state may include, e.g., formation of a free radical and/or cationic and/or anionic charge. A transformation of bonding configurations may be achieved, e.g., by promoting a chemical reaction such as chemical reduction. Accordingly a chemical transformation herein may also include bond rearrangement and/or chemical transformation through breaking and reforming of bonds. A chemical transformation herein may also include selective isomerization, such as, for a given molecule or molecules, the formation of the complementary stereo enantiomer (i.e. the formation of a stereoisomer of a given molecule that is not superimposable with respect to the original molecule). Finally, a chemical transformation may entail any of those defined above, occurring in one or more locations of a molecule; for example, a macromolecule consisting of one or more active sites within which a said chemical transformation takes place.

In addition, the chemical transformation noted above may occur by the coupling of the surface-bound electric field of the plasmon mode with the molecule's vibrations. That is, it may be understood that coupling refers to interaction of the surface-bound electric field of the plasmon mode with the molecule to achieve some level of vibrational resonance, thereby causing a chemical transformation within the molecule as noted herein.

Referring again to Table 1, the selective nature of the chemical transformation as defined herein is afforded by the combined effect of resonant coupling of the SPP with the electronic, vibrational, or phonon transitions of the enantiomer, the propagational polarization of the SPP's electric field, and the dipole or multipole phase vortices generated by the ortho or para combinations.

Structured surfaces, such as arrayed holes and nanowires and metallic mesostructures may exhibit SPPs ranging from ultraviolet to the infrared and microwave regions of the electromagnetic spectrum. Very large near-field effects may arise from resonant coupling between an external field and the SPPs in these systems. Using ab initio and classical (Maxwell's equations) levels of theory, one exemplary embodiment of this disclosure relates to a free-standing (3-D) structure with spatial chirality that can now be tailored to evince SPPs with propagational polarization whose frequency can be made to be resonant with either the electronic, vibrational, or phonon transitions of a chiral molecule.

Figure 3:
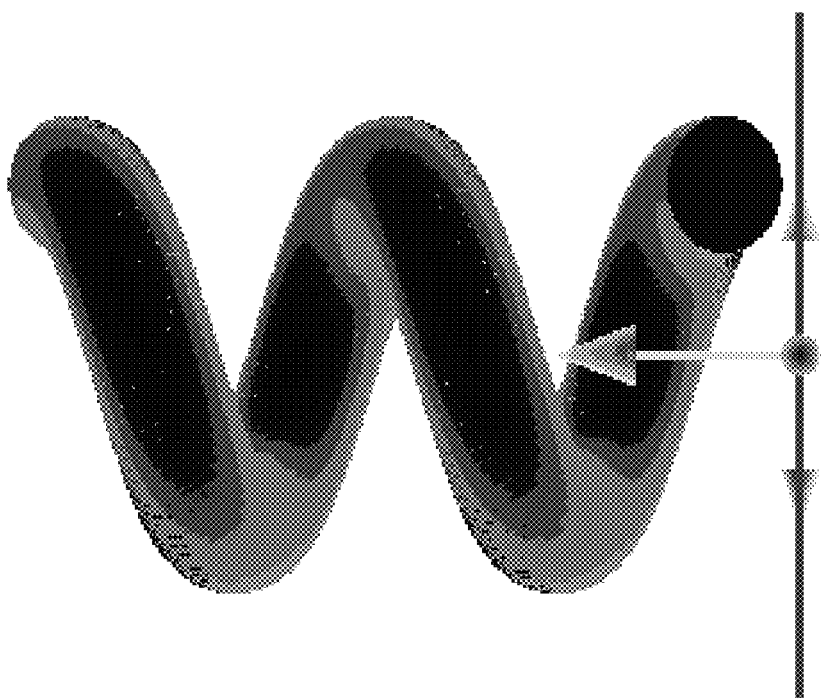
FIG. 3 is a three-dimensional chiral structure consisting of a gold helical wire (right handed relative to the direction of light propagation), having a wire diameter of 40 nm, a helix radius of 50 nm, and extending 200 nm in length.

An exemplary chiral plasmonic structure of the present disclosure is the helical gold nano-wire illustrated in FIG. 3. Single helices or arrays of helices of selected handedness (right- or left-handed) can be fabricated by direct laser writing (DLW) into a block of photoresist polymer, followed by electrochemical deposition of a metal, such as gold, and removal of the residual polymer using plasma etching. Arrays of helical structures of uniform chirality may also be grown as amorphous silica structures and then coated with a metal using vapor deposition. Regardless of the method employed to fabricate such chiral structures, the features of the present disclosure will now be described via the representative model structure of FIG. 3 and the results of classical, finite difference time domain (FDTD) simulations.

Figure 4A:
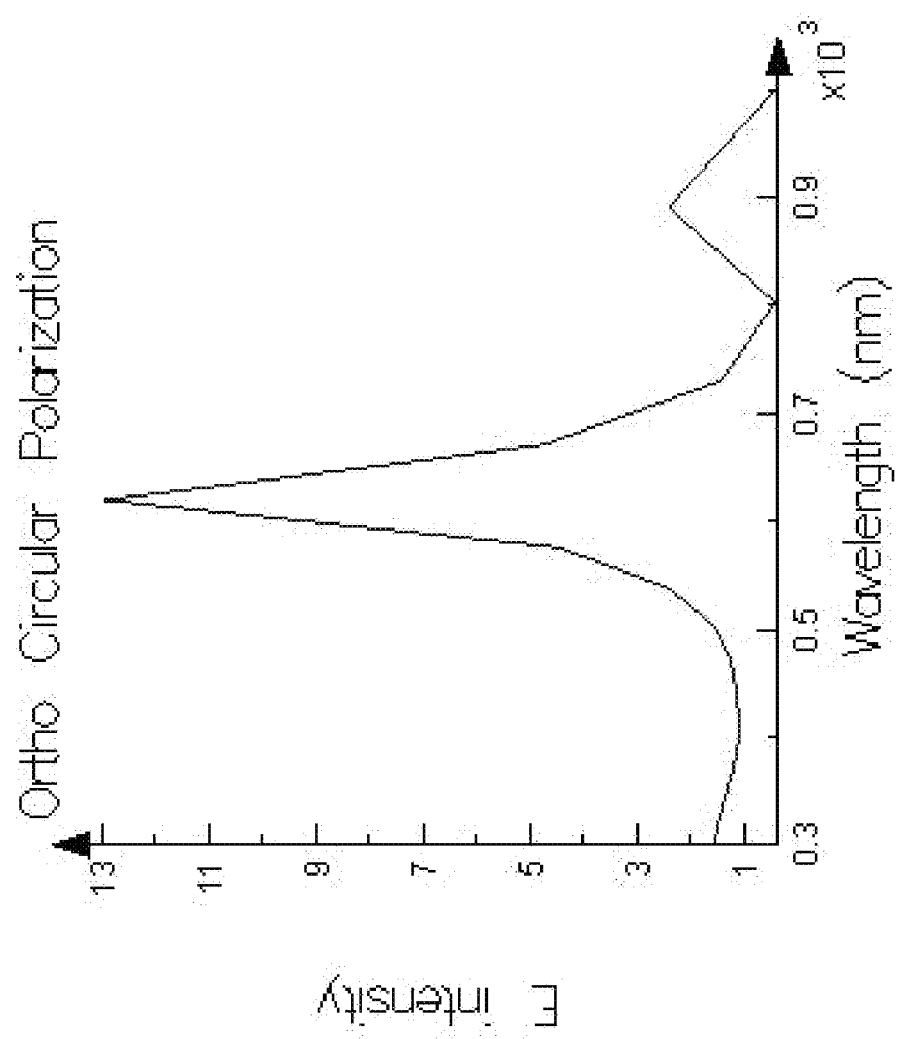
FIG. 4A is the total field resonances predicted from the FDTD model in FIG. 3, showing that the helical wire yields a principal resonance from ortho circular polarization at 620 nm.
Figure 4B:
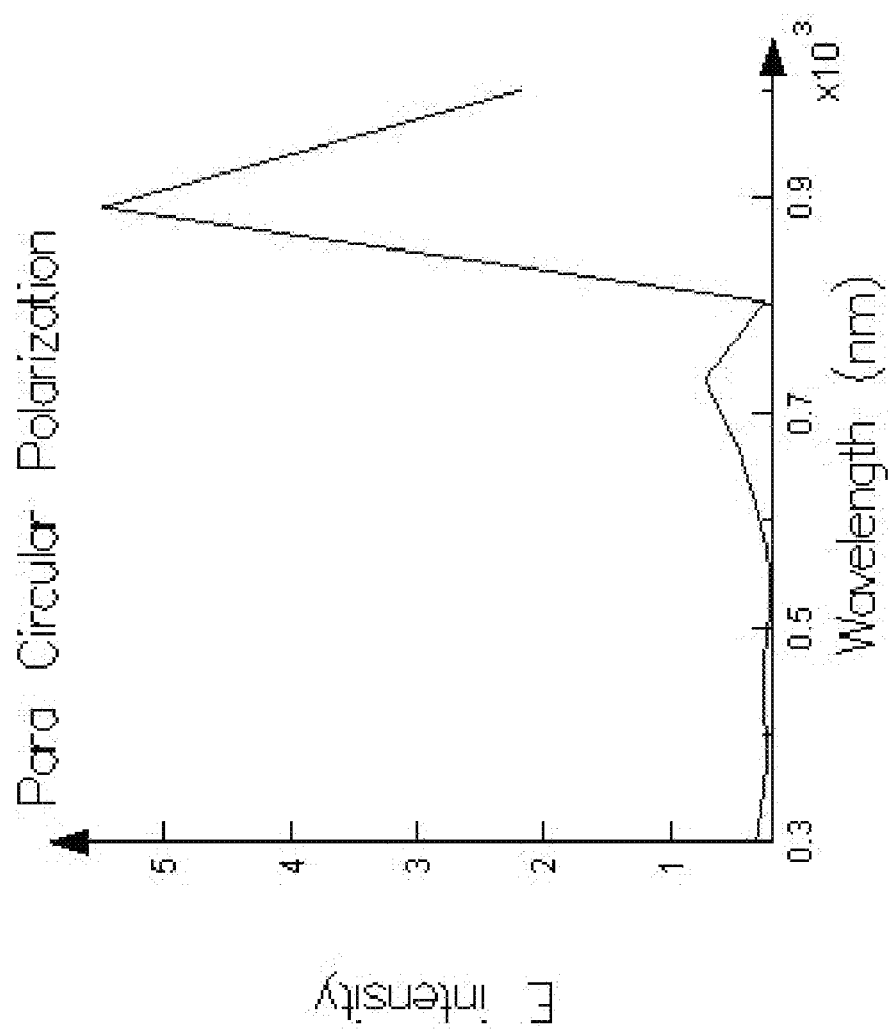
FIG. 4B is the total field resonances predicted from the FDTD model in FIG. 3, showing that the helical wire yields a principal resonance from para circular polarization at 891 nm.
Figure 5A:
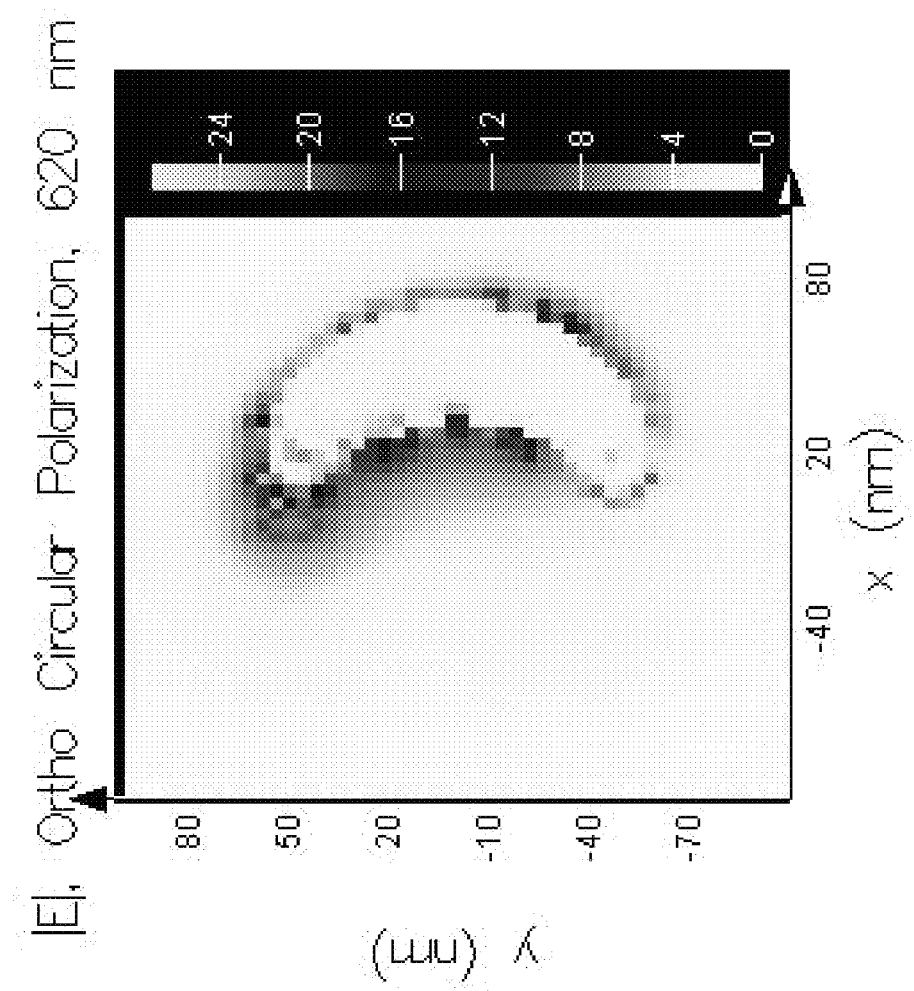
FIG. 5A is a contour map of the magnitude of the electric field in the XY plane, showing excitation of SPPs on the surface of the helical wire on resonance (620 nm) for ortho circular polarization.
Figure 5B:
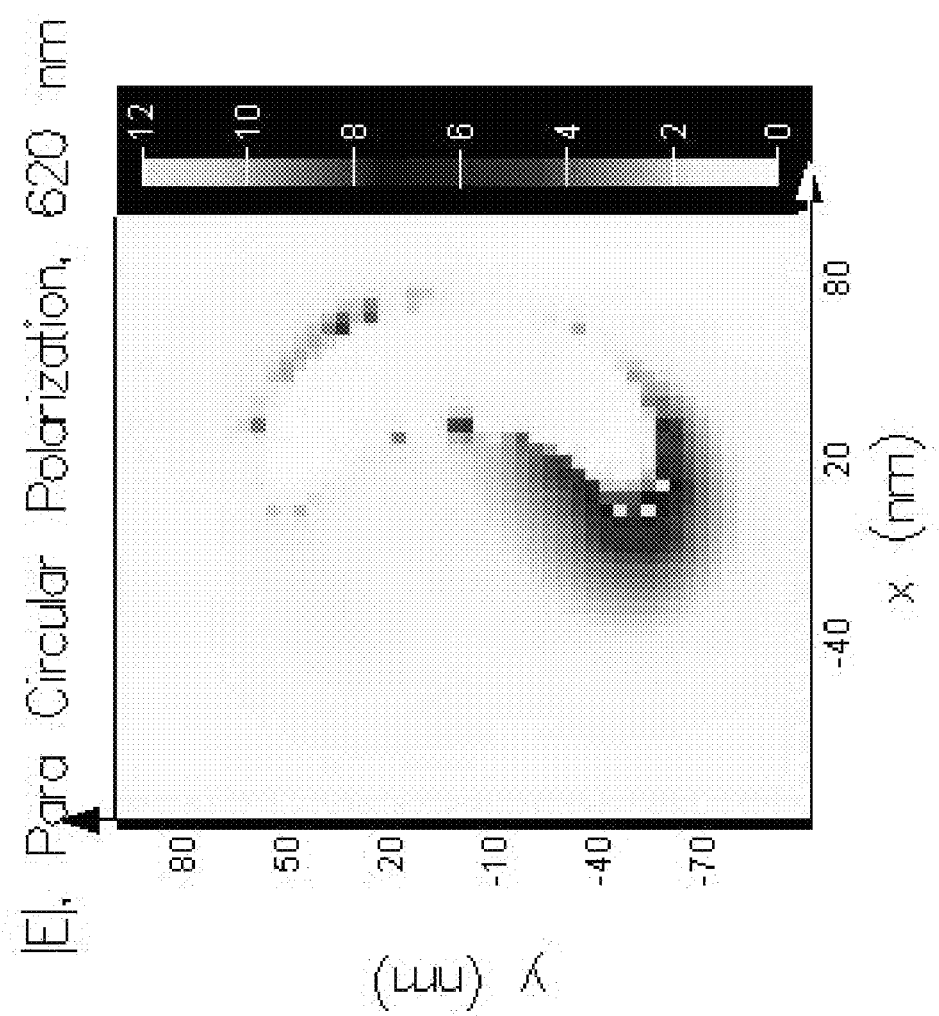
FIG. 5B is a contour map of the magnitude of the electric field in the XY plane, showing excitation of SPPs on the surface of the helical wire on resonance (620 nm) for para circular polarization.
Figure 5C:
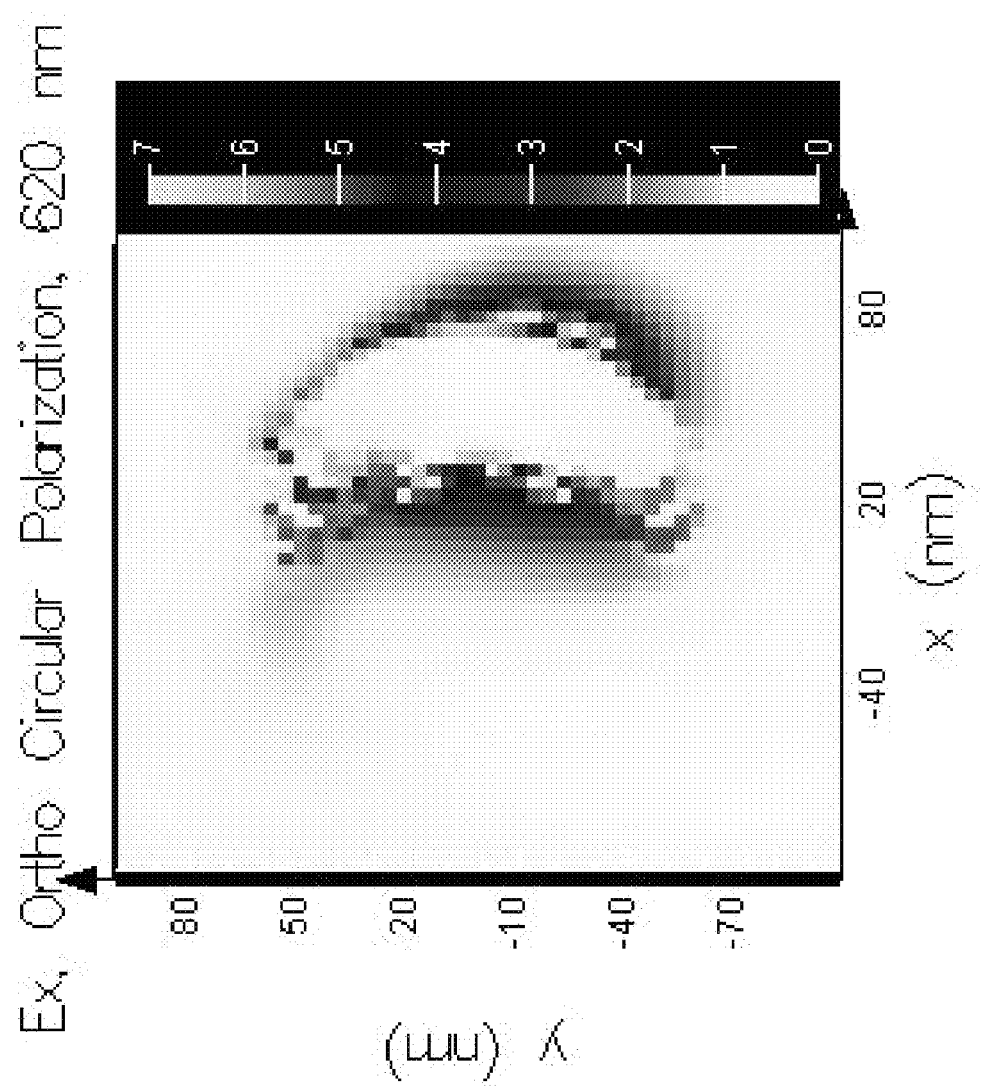
FIG. 5C is a contour map showing the gradients of the x-component of the electric field in the XY plane of the helical wire on resonance (620 nm) for ortho circular polarization.
Figure 5D:
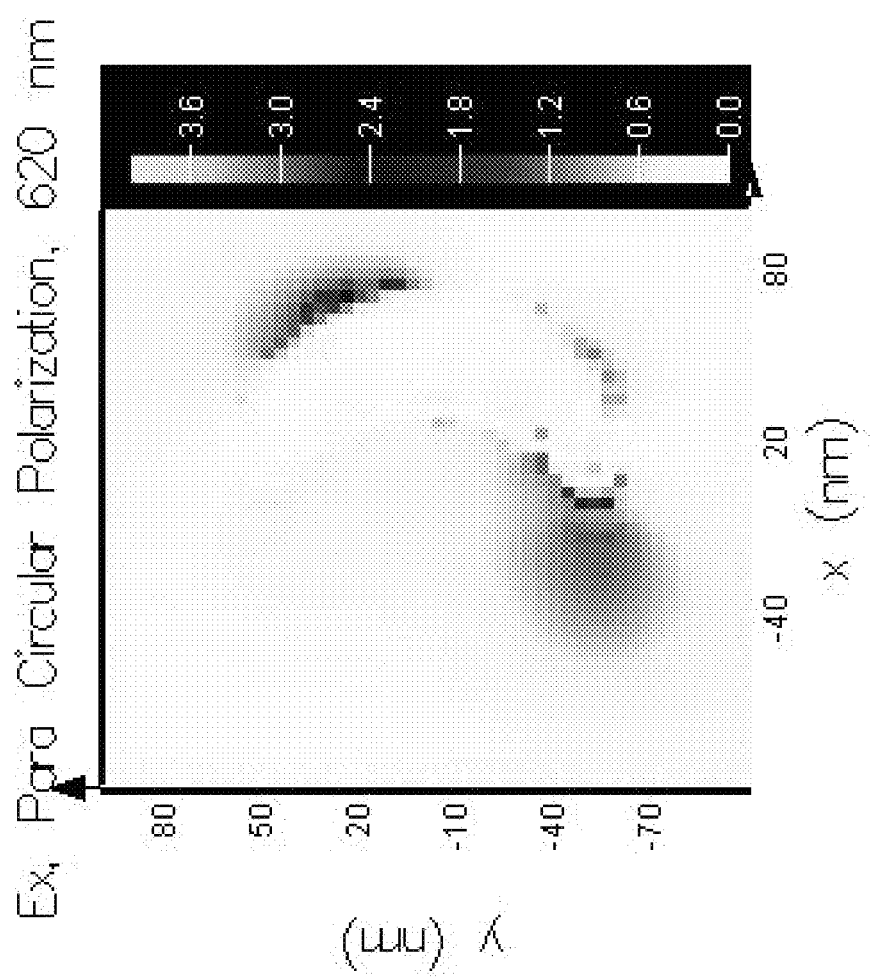
FIG. 5D is a contour map showing the gradients of the x-component of the electric field in the XY plane of the helical wire on resonance (620 nm) for para circular polarization.
Figure 5E:
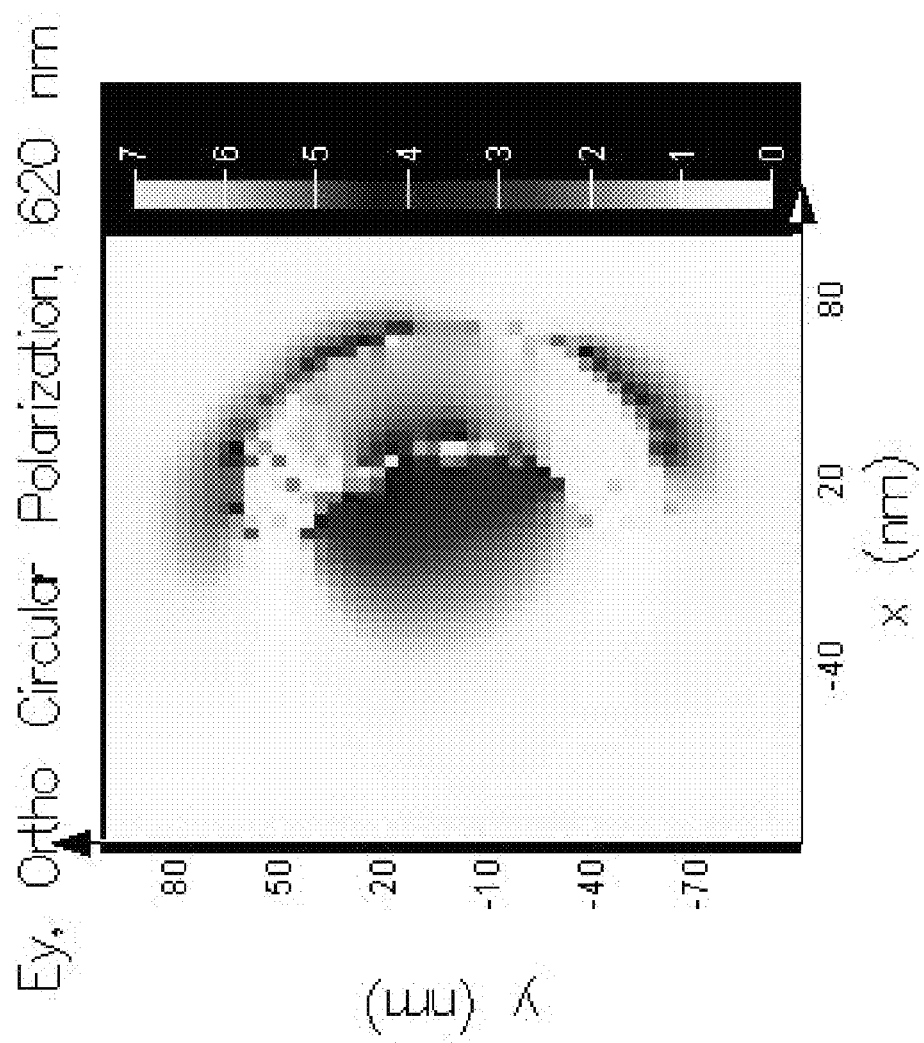
FIG. 5E is a contour map showing the gradients of the y-component of the electric field in the XY plane of the helical wire on resonance (620 nm) for ortho circular polarization.
Figure 5F:
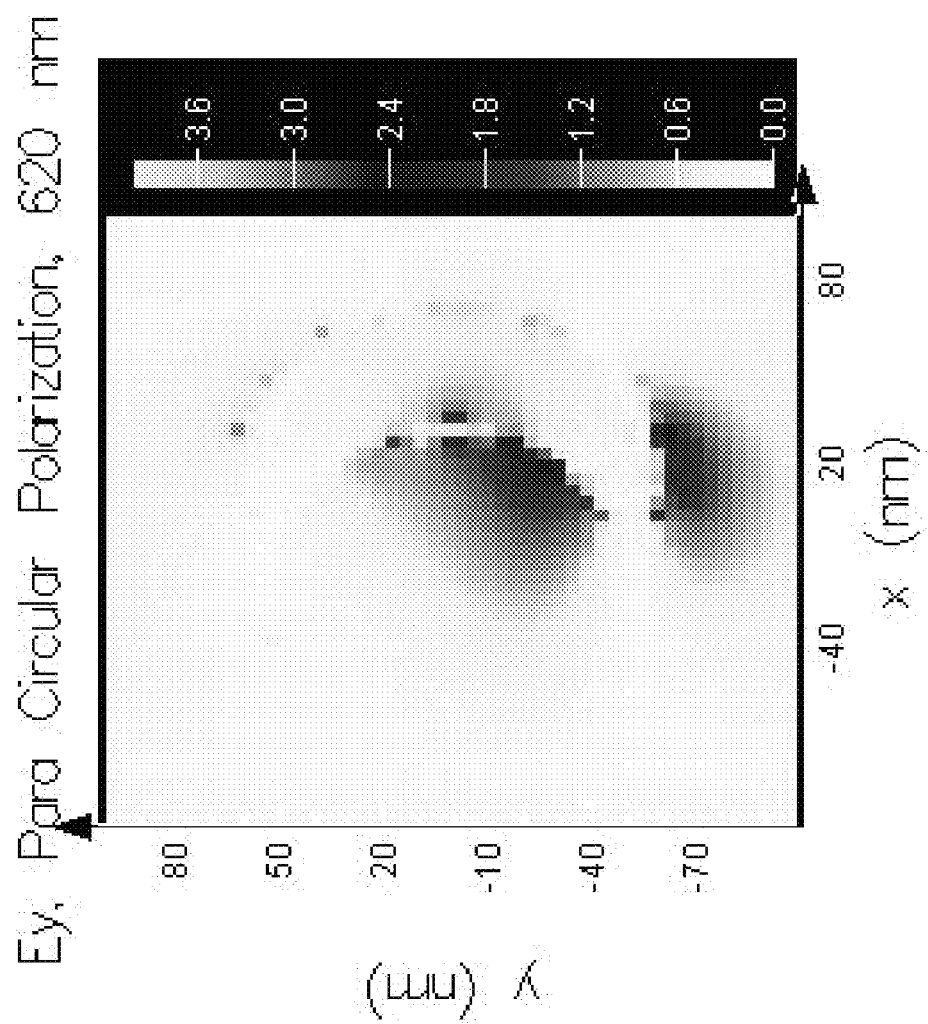
FIG. 5F is a contour map showing the gradients of the y-component of the electric field in the XY plane of the helical wire on resonance (620 nm) for para circular polarization.

An external field of given spectral width (300-1000 nm) is propagated along the positive z axis of a helical gold wire (40 nm wire diameter×200 nm helix length×50 nm helix radius) with circular polarization (CP) in the same direction as the handedness of the helix; that is, the ortho combination comprising right-handed CP and a right-handed helix. The total field resonances predicted for this interaction are illustrated in FIGS. 4A and 4B, which show a peak resonance at 620 nm for the ortho combination and at 891 nm for the para combination. FIG. 5A illustrates a contour map of the magnitude of the electric field in the XY plane derived from the FDTD simulation, showing excitation of SPPs on the surface of the helical wire on resonance (620 nm) for the ortho combination. In contrast, the para combination yields electric field contours that are quite different from the ortho combination, as shown in FIG. 5B. These differences are further revealed by mapping separately the x- and y-components of the electric field (Ex, Ey) in each case as illustrated in FIGS. 5C, 5D, 5E, and 5F for the ortho and para combinations.

Figure 6A:
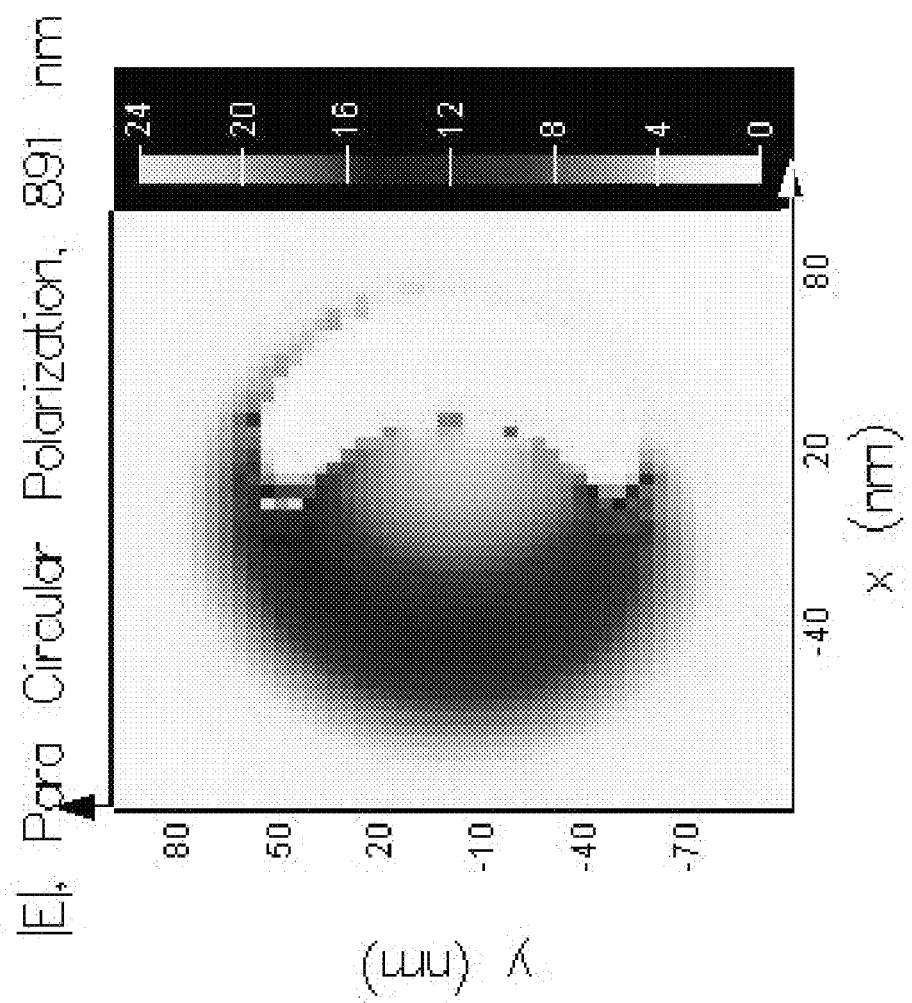
FIG. 6A is a contour map of the magnitude of the electric field in the XY plane, showing excitation of SPPs on the surface of the helical wire on resonance (891 nm) for para circular polarization.
Figure 6B:
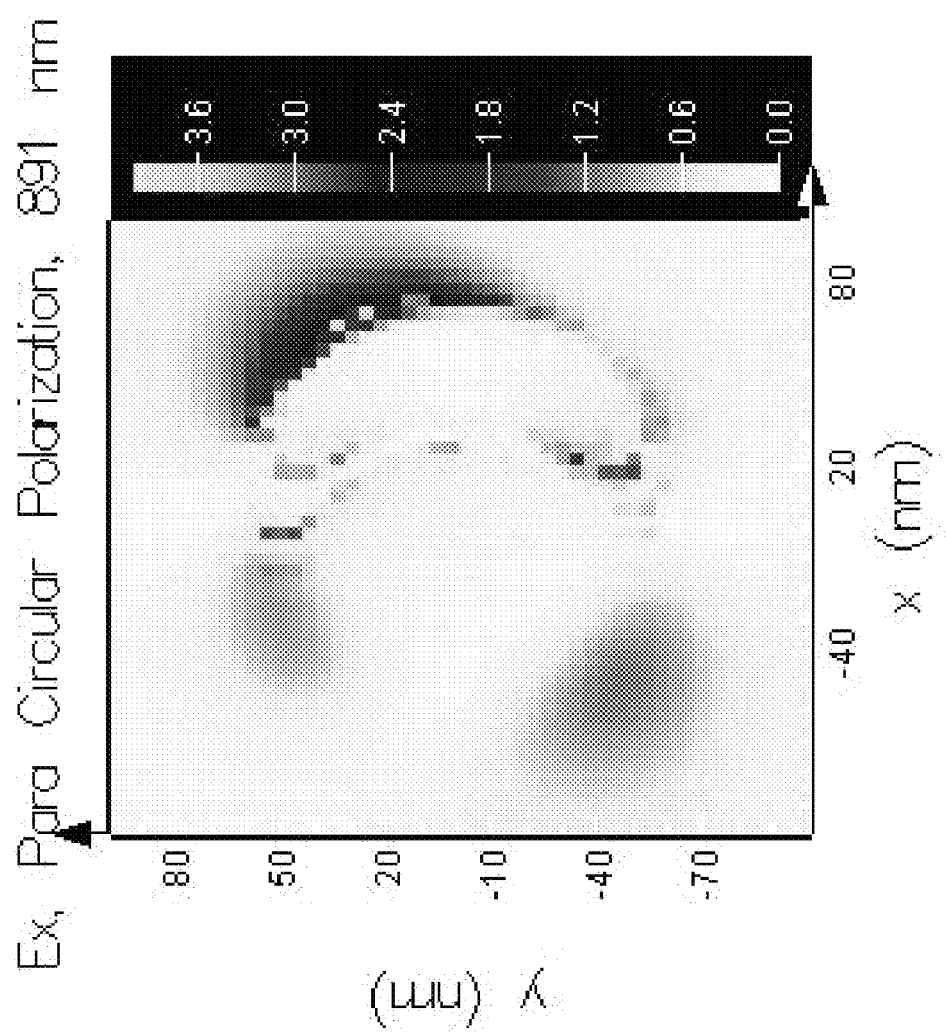
FIG. 6B is a contour map showing the gradients of the x-component of the electric field in the XY plane of the helical wire on resonance (891 nm) for para circular polarization.
Figure 6C:
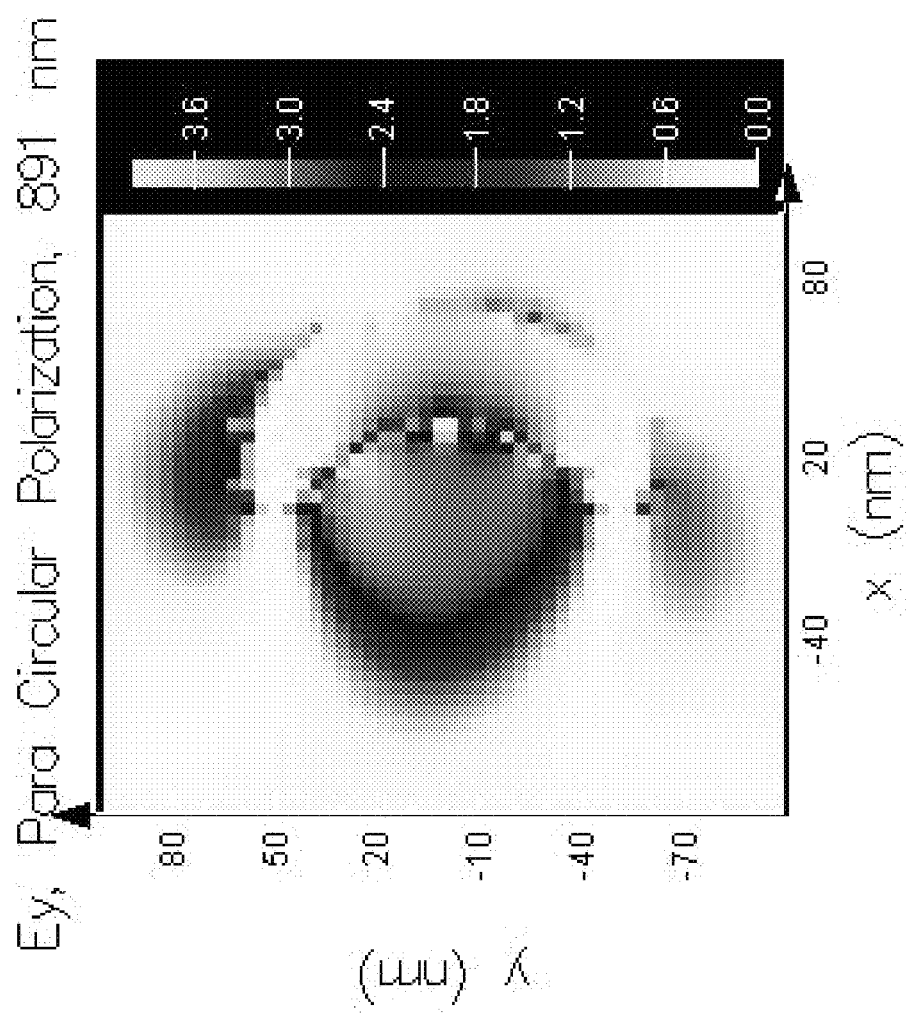
FIG. 6C is a contour map showing the gradients of the y-component of the electric field in the XY plane of the helical wire on resonance (891 nm) for para circular polarization.

It is further illustrated in FIG. 6 that SPPs are elicited from the helical wire at the peak resonance of the para combination (891 nm), leading to contour maps of the total electric field and its x- and y-components that exhibit unique intensity patterns (i.e., vortices) neither realized for the para combination off resonance (620 nm) nor the ortho combination on resonance. As an exemplary model of a chiral plasmonic structure, therefore, the helical metal wire of the present disclosure is demonstrated to elicit SPPs at distinct resonance frequencies (wavelengths) that depend on the ortho and para combinations, as defined in Table 1, and the feature dimensions of the helix. The vortices associated with the localized electric fields of these SPPs derive from the handedness of the external field and that of the chiral structure.

For specified molecules (e.g. macromolecules), especially biological proteins, the pattern of electron density is often studied in terms of isodensity contour surfaces which confer all molecular information and forms the basis of molecular shape analysis. Large scale shape features, including long-range chirality, emerge from these studies. It is to be recognized that the utility of the present disclosure may now be directed toward performing surface plasmon-mediated chemical work on, or detection of, macromolecules with long-range chirality proportionate in scale to the chiral plasmonic structure. This proportionate scaling may be utilized in order that the long-range chirality of the macromolecule defined by the pattern of electron density couples with the propagational polarization of the SPP elicited in the chiral plasmonic structure. Selectivity of a chemical transformation, or detection, is thereby afforded by the enhanced coupling that occurs between the strong, localized electric field of the SPP and electronic, vibrational, or phonon transitions in the macromolecule, when the propagational polarization of the coupled SPP is in the same direction as the long-range chirality (i.e., optical activity) of the macromolecule.

While not limiting the utility of the present disclosure to any one or group of chemical transformations, or detection of any one or group of macromolecules with long-range chirality, the following exemplary cases are representative and contemplate the utility of chiral plasmonic structures for surface-plasmon-mediated transformation or detection:

1. Catalysis of reactions on functional groups of helical polypeptides.
2. Selective detection of α- and β enantiomers of helical polypeptides.
3. Chemical transformation or detection of chiral capsomeres making-up the capsids of viruses (e.g., papillomavirus).
4. Enantioselective binding, or detection of binding, between chiral ligands and chiral receptors in biological macromolecules.
5. Enantioselective inhibition of binding, or detection of binding inhibition, between chiral ligands and chiral receptors in biological macromolecules.
6. Catalytically accelerated enantioselective transformation of chiral ligands by natural enzymes.

While detection and transformation of selected chiral molecules in the presence of SPP enhanced and circularly polarized fields has been the focus of the above referenced applications, another useful detection scheme is also contemplated herein.

More specifically, the present disclosure also contemplates detection of the proportion of the two enantiomers in a racemic mixture. The method to characterize relatively small quantities of a mixture may now be achieved by spreading a selected sample thin and counting the instances of each enantiomer. In contrast to the methods described earlier, these imaging approaches may be optimized if the chiral structures are relatively smaller than the sample molecules. SPP's in this case are not required to be sharply tuned to spatially or harmonically match molecule resonances.

Spatially resolved imaging in which structural chirality is mapped for any sample or mix can be accomplished in two ways. In both, the detection scheme depends on preferential transmission of the incident circularly polarized radiation when the sample molecules are of the same rotational sense. The first imaging scheme involves a scanned imaging technique. Chiral structures may be grown on or in the tip of an NSOM (near-field scanning optical microscope) probe, such that they polarize radiation exiting the probe and enhance fields in close proximity to the tip. The NSOM tip may have two chambers, each bearing chiral structures with opposing sense. This chiral NSOM tip can be scanned over a sample surface to create two time-multiplexed images. By examining the difference of the images from each half of the tip, the result will be enhanced. A second method involves arraying chiral structures in a film to be placed in the transmission path of the sample and taking a "snapshot" image of the transmitted radiation. This snapshot may either be compared to a control, or to a second film with oppositely twisted chiral structures for an image of the transmission difference. Automated signal processing techniques may be used for quick statistical analysis of the resultant images.

Another imaging technique is contemplated. Canalization regimes in wire arrays exist in which subwavelength details are transported from the near field into the far field. If the "wires" themselves are chiral, informative polarization interactions may occur and be exploited further for chirality imaging of denser racemic mixes.

The present disclosure therefore contemplates one or more of the following structures or processing methodologies which may be present alone or in any combination:

A structure, or an array of such a structure, possessing spatial chirality (handedness) capable of eliciting surface plasmon modes at selected frequencies that exhibit propagational polarization when excited by a circularly polarized external source and/or the vibrational dipole created by a molecule or molecules adsorbed on said metal dielectric surface, wherein said surface-bound electric field is capable of coupling with electronic, vibrational, or phonon transitions of said molecule, wherein the propagational polarization of said surface-bound electric field of the plasmon created by said chiral structure couples with the spatial chirality of said molecule, and wherein said molecule undergoes a chemical transformation and/or its detection is facilitated.

A structure, or an array of such a structure, possessing spatial chirality (handedness) wherein the circular polarization of the external field is in the same direction as the chirality of said metal-dielectric structure, thereby eliciting surface plasmon modes at selected frequencies that exhibit propagational polarization, and further causing the electric field components of the surface plasmon modes to exhibit gradients and/or vortices near the surface of the said chiral structure.

A structure, or an array of such a structure, possessing spatial chirality (handedness) wherein the circular polarization of the external field is in the opposite direction as the chirality of said metal-dielectric structure, thereby eliciting surface plasmon modes at selected frequencies that exhibit propagational polarization, and further causing the electric field components of the surface plasmon modes to exhibit gradients and/or vortices near the surface of the said chiral structure that are different from those created above.

A structure capable of causing a chemical transformation comprising a material containing at least one metal and one dielectric.

A structure capable of causing a chemical transformation wherein the structure comprises a three-dimensional wire helix or an array of three-dimensional wire helices.

A structure capable of causing a chemical transformation wherein the magnitude of the coupling between the surface-bound electric field of the plasmon mode is sufficiently strong to induce a molecule, preferably a macromolecule of similar scale as the structure, adsorbed on the surface of the structure, or an active site on said molecule, to undergo bond rearrangement in a selective manner depending on the propagational polarization of the surface plasmon and the long-range spatial chirality of the molecule.

A structure capable of causing a chemical transformation wherein the magnitude of the coupling between the surface-bound electric field of the plasmon mode is sufficiently strong to induce a molecule, preferably a macromolecule of similar scale as the structure, adsorbed on the surface of the structure, or an active site on said molecule, to undergo bond breaking and bond reforming in a selective manner depending on the propagational polarization of the surface plasmon and the long-range spatial chirality of the molecule.

A structure capable of causing a chemical transformation wherein the magnitude of the coupling between the surface-bound electric field of the plasmon mode is sufficiently strong to induce a molecule, preferably a macromolecule of similar scale as the structure, adsorbed on the surface of the structure, or an active site on said molecule, to transform into a metastable state in selective manner depending on the propagational polarization of the surface plasmon and the long-range spatial chirality of the molecule.

A structure capable of causing a chemical transformation wherein the magnitude of the coupling between the surface-bound electric field of the plasmon mode is sufficiently strong to induce a molecule, preferably a macromolecule of similar scale as the structure, adsorbed on the surface of the structure, or an active site on said molecule, to undergo isomerization in a selective manner depending on the propagational polarization of the surface plasmon and the long-range spatial chirality of the molecule.

A process for supplying a metal dielectric structure, or an array of such a structure, possessing spatial chirality (handedness) capable of eliciting surface plasmon modes at selected frequencies that exhibit propagational polarization when excited by a circularly polarized external source and/or the vibrational dipole created by a molecule or molecules adsorbed on said metal dielectric surface, wherein said surface-bound electric field is capable of coupling with electronic, vibrational, or phonon transitions of said molecule, wherein the propagational polarization of said surface-bound electric field of the plasmon created by said chiral structure couples with the spatial chirality of said molecule, and wherein said molecular transitions are detected as absorption and/or change in transmission.

The process as noted above, wherein the absorption and/or change in transmission is achieved with a photon detector.

The process as noted above, where the coupling between the surface-bound electric field of the plasmon mode under propagational polarization and the said vibrational or phonon transitions are detected by surface enhanced Raman spectroscopy (SERS).

The process as noted above, where the coupling between the surface-bound electric field of the plasmon mode under propagational polarization and the said electronic, vibrational or phonon transitions are detected by surface plasmon resonance spectroscopy (SPRS).

The process as noted above where the coupling between the surface-bound electric field of the plasmon mode under propagational polarization and the said vibrational or phonon transitions are detected as a change in heat flow relative to a reference state utilizing a thermal detector; for example, the measurement apparatus typically employed in a differential calorimeter.

A process for spatially resolving an image of the individual enantiomers of a racemic mixture with the purpose of statistically characterizing the proportion and position of each enantiomer.

The process as noted above, where the structure for characterizing the racemic mix comprises an NSOM tip with chiral, plasmonic field enhancing structure or structures.

What is claimed is:

1. A structure comprising:
a metal dielectric possessing spatial chirality capable of eliciting surface plasmon modes at selected frequencies to provide a surface bound electric field that exhibits propagational polarization when excited by a circularly polarized external source and/or a vibrational dipole created by a molecule adsorbed on said metal dielectric surface, said molecule having a spatial chirality;
wherein said surface-bound electric field is capable of coupling with electronic, vibrational, or phonon transitions of said molecule;
wherein the propagational polarization of said surface-bound electric field of the plasmon created by said chiral metal dielectric couples with the chirality of said molecule, and wherein said molecule undergoes a chemical transformation.

2. The structure of claim 1 wherein the circular polarization of the external field is in the same direction as the chirality of said metal-dielectric structure.

3. The structure of claim 1 wherein the circular polarization of the external field is in the opposite direction as the chirality of said metal-dielectric structure.

4. The structure of claim 1 wherein said metal dielectric comprises a three-dimensional wire helix.

5. The structure of claim 1 wherein the coupling between the surface bound electric field of the plasmon mode is sufficiently strong to induce a molecule adsorbed on the surface of said structure to undergo bond rearrangement.

6. The structure of claim 1 wherein the coupling between the surface bound electric field of the plasmon mode is sufficiently strong to induce a molecule adsorbed on the surface of the structure to undergo bond breaking and bond reforming.

7. The structure of claim 1 wherein the coupling between the surface bound electric field of the plasmon mode is sufficiently strong to transform said molecule adsorbed on the surface of the structure into a metastable state.

8. The structure of claim 7 wherein said metastable state of said molecule comprises the presence of a free radical, cation or anion.

9. The structure of claim 1 wherein the coupling between the surface-bound electric field of the plasmon mode is sufficiently strong to induce a molecule adsorbed on the surface of the structure to undergo isomerization.

10. A process for causing a chemical transformation of a molecule on the surface of structure comprising:
supplying a metal dielectric possessing spatial chirality capable of eliciting surface plasmon modes at selected frequencies to provide a surface bound electric field that exhibits propagational polarization when excited by a circularly polarized external source and/or a vibrational dipole created by a molecule adsorbed on said metal dielectric surface, said molecule having a spatial chirality;
coupling said surface bound electric field with said molecule on the surface of said metal dielectric structure such that the propagational polarization of the surface bound electric field couples with the chirality of said molecule;
chemically transforming said molecule.

11. The process of claim 10 wherein said molecule having spatial chirality comprises two or more chiral molecules and said chemical transformation comprises a selective chemical transformation of at least one of said chiral molecules.

12. The process of claim 10 wherein the circular polarization of the external field is in the same direction as the chirality of said metal-dielectric structure.

13. The process of claim 10 wherein the circular polarization of the external field is in the opposite direction as the chirality of said metal-dielectric structure.

14. The process of claim 10 wherein said metal dielectric comprises a three-dimensional wire helix.

15. The process of claim 10 wherein the coupling between the surface bound electric field of the plasmon mode is sufficiently strong to induce a molecule adsorbed on the surface of said structure to undergo bond rearrangement.

16. The process of claim 10 wherein the coupling between the surface bound electric field of the plasmon mode is sufficiently strong to induce a molecule adsorbed on the surface of the structure to undergo bond breaking and bond reforming.

17. The process of claim 10 wherein the coupling between the surface bound electric field of the plasmon mode is sufficiently strong to transform said molecule adsorbed on the surface of the structure into a metastable state.

18. The process of claim 17 wherein said metastable state of said molecule comprises the presence of a free radical, cation or anion.

19. The process of claim 10 wherein the coupling between the surface-bound electric field of the plasmon mode is sufficiently strong to induce a molecule adsorbed on the surface of the structure to undergo isomerization.

20. The process of claim 10 where the coupling between the surface-bound electric field of the plasmon mode under propagational polarization and the said vibrational or phonon transitions are detected by surface enhanced Raman spectroscopy.

21. The process of claim 10 where the coupling between the surface-bound electric field of the plasmon mode under propagational polarization and the said electronic, vibrational or phonon transitions are detected by surface plasmon resonance spectroscopy.

22. The process of claim 10 above where the coupling between the surface-bound electric field of the plasmon mode under propagational polarization and the said vibrational or phonon transitions are detected as a change in heat flow relative to a reference state utilizing a thermal detector.

23. A process for spatially resolving images of individual enantiomers of a racemic mixture:
supplying a metal dielectric possessing spatial chirality capable of eliciting surface plasmon modes at selected frequencies to provide a surface bound electric field that exhibits propagational polarization when excited by a circularly polarized external source and/or a vibrational dipole created by a racemic mixture of molecules adsorbed on said metal dielectric surface, said molecules having spatial chirality;
coupling said surface bound electric field with said molecule on the surface of said metal dielectric structure such that the propagational polarization of the surface bound electric field couples with the chirality of said molecule;
detecting the proportion of enantiomers in said racemic mixture.

\* \* \* \* \*